United States Patent [19]
Schellenberg et al.

[11] Patent Number: 6,020,373
[45] Date of Patent: Feb. 1, 2000

[54] CHELATE DERIVATIVES AS PROTECTORS AGAINST TISSUE INJURY

[75] Inventors: Karl A. Schellenberg, Virginia Beach; James Shaeffer; Frank A. Lattanzio, Jr., both of Chesapeake, all of Va.

[73] Assignee: Eastern Virginia Medical School, Norfolk, Va.

[21] Appl. No.: 08/845,247

[22] Filed: Apr. 21, 1997

Related U.S. Application Data

[63] Continuation-in-part of application No. 08/546,562, Oct. 20, 1995, abandoned.

[51] Int. Cl.$^7$ .................................................. A61K 31/225
[52] U.S. Cl. ......................... 514/547; 514/252; 514/255; 514/551; 514/563; 544/357; 544/385; 560/169; 562/564
[58] Field of Search ............................ 562/564; 544/357, 544/385; 514/252, 255, 551, 563, 547; 560/169

[56] References Cited

U.S. PATENT DOCUMENTS

| | | |
|---|---|---|
| 3,281,322 | 10/1966 | Ashmead et al. . |
| 3,499,966 | 3/1970 | Dwyer et al. . |
| 3,810,848 | 5/1974 | Chapurlat et al. . |
| 3,810,872 | 5/1974 | Chapurlat et al. . |
| 3,810,873 | 5/1974 | Chapurlat et al. . |
| 3,810,888 | 5/1974 | Chapurlat et al. . |
| 4,352,751 | 10/1982 | Wieder et al. . |
| 4,432,907 | 2/1984 | Wieder et al. . |
| 4,673,688 | 6/1987 | Murashige et al. . |
| 4,772,563 | 9/1988 | Evangelista et al. . |
| 4,814,457 | 3/1989 | Stapersma . |
| 4,879,234 | 11/1989 | Cordes et al. . |
| 5,137,711 | 8/1992 | Weber ......................................... 424/9 |
| 5,242,901 | 9/1993 | Speyer ....................................... 514/8 |
| 5,370,877 | 12/1994 | Rosenberg et al. . |
| 5,744,455 | 4/1998 | Speyer ..................................... 514/34 |

FOREIGN PATENT DOCUMENTS

| | | |
|---|---|---|
| 91/15467 | 4/1991 | WIPO . |
| 97/14413 | 4/1997 | WIPO . |

*Primary Examiner*—Michael L. Shippen
*Attorney, Agent, or Firm*—Banner & Witcoff, Ltd.

[57] ABSTRACT

Derivatives useful in the protection of living organisms against damage due to free radical reactions derived from methoxypolyethylene glycols (MPEG), which are modified by chemically attaching chelating groups in an amide or amine linkage to the nonmethyl end of the polymer. Such chelating groups include ethylene-diamine tetraacetic acid (EDTA), diethylene triamine pentaacetic acid (DTPA), and ethylene glycol aminoethyl ether tetraacetic acid (EGTA), and pharmacologically acceptable salts or esters thereof.

15 Claims, 7 Drawing Sheets

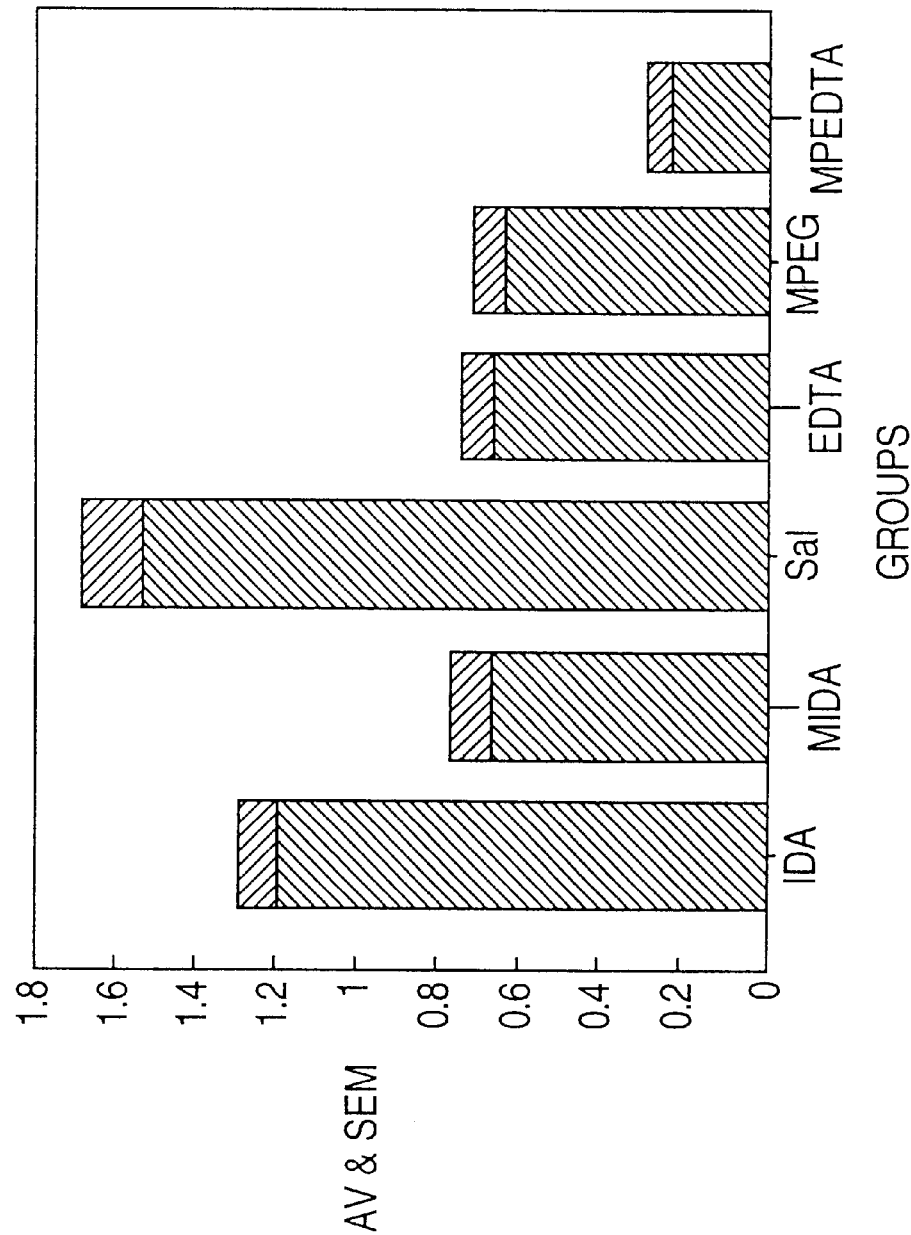

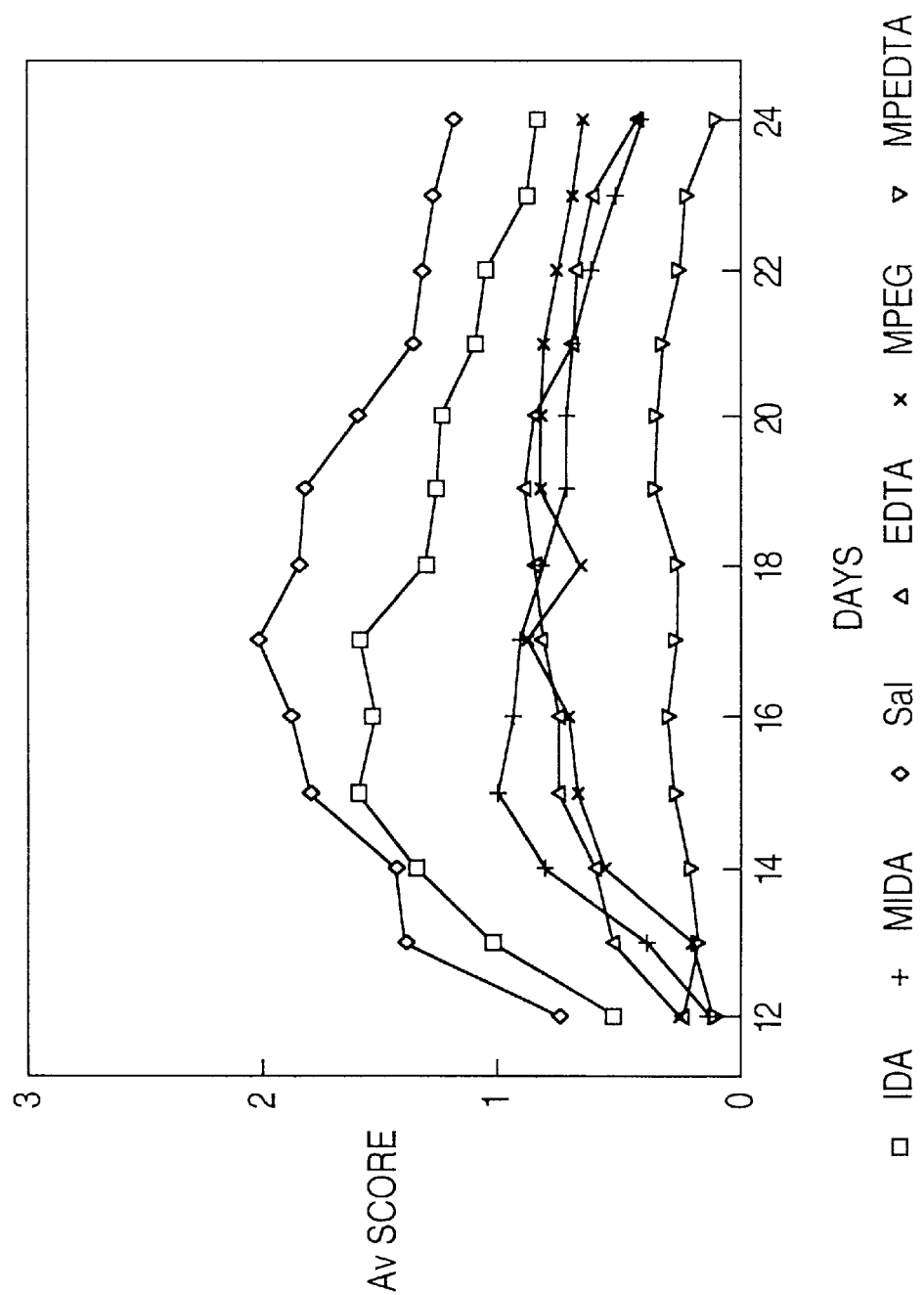

CHELATE DERIVATIVES AS PROTECTORS AGAINST TISSUE INJURY

This application is a continuation in part of prior application Ser. No. 08/546,562, filed Oct. 20, 1995, now abandoned.

FIELD OF INVENTION

The present invention is directed to substances useful in the protection of living organisms against damage due to free radical reactions.

BACKGROUND OF INVENTION

Iron is involved in the pathogenesis of free radical tissue injury following inflammation. Activated leukocytes thus produce superoxide radicals which undergo dismutation to hydrogen peroxide and oxygen, and simultaneously reduce iron in ferritin. $Fe^{++}$, in turn, reacts with hydrogen peroxide, producing the destructive hydroxyl radical. The radical reactions may be summarized:

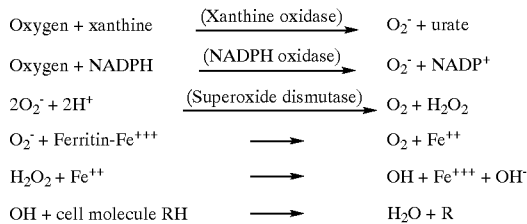

The presence of free iron is thus essential for the tissue damage, and removal of the metal from the system by chelation should reduce the tissue injury.

Iron chelators, including deferoxamine (DEF), have shown some effectiveness in reducing tissue injury, such as myocardial ischemia-reperfbsion injury. DEF must be given parenterally, but its toxicity and rapid excretion limit its effectiveness. By covalently linking DEF with high molecular weight substances, such as hydroxyethylstarch, the circulation lifetime was increased and toxicity decreased (Hallaway, et al., *Proc. Nat. Acad Sci. USA*, 86:10108, 1989). Other iron chelators have been explored in an effort to reduce tissue injury from free radicals (Voest, et al., *Ann. Intern. Med*, 120:490–499, 1994).

Polyethylene glycol (PEG) and its monomethyl ether (MPEG) have also been found to reduce tissue injury, although the mechanism is obscure. PEG is an amphiphilic polymer $H(OCH_2CH2)_nOH$ that consists of a mixture of homologs with a range of similar molecular weights. Thus, MPEG 350 possesses an average molecular weight 350, and consists of a mixture of homologs with n=4 to 9, median n=7. The low molecular weight polymers PEG 200–600 are absorbed through the gastrointestinal tract when ingested orally and excreted unchanged in the urine. PEG is absorbed along with water directly through the intestinal mucosal cell membrane.

PEG 200–600, being nontoxic and biologically inert, has often been used as a vehicle for administration of drugs insoluble in water. In several investigations, the PEG vehicle alone was empirically found to exhibit significant biological activity, leading to further studies of low molecular weight PEG. As examples, PEG 400, when given intraperitoneally (IP) either before or shortly after x-irradiation of mice, conferred significant protection against lethality and morbidity (Shaeffer and Schellenberg, *Int. J. Radiat. Oncol. Biol. Phys.*, 10:2329, 1984; Shaeffer, et al., *Radiat. Res.*, 107:125, 1986). PEG 300 IP was shown to reduce the CNS sequelae of experimental concussive brain injury (Clifton, et al., *J. Neurotrama*, 6:71, 1989).

PEG with a molecular weight around 400 is thus a uniquely nontoxic substance that exhibits a protective effect against injury to tissues. However, PEG with a molecular weight greater than 700 is not absorbed through the GI tract. The mechanism of the protective action of low molecular weight PEG has not been established, but probably involves interaction of PEG with the surface of lipid membranes or protein components. PEG aggregates near cell membranes, reduces water polarity at membrane surfaces, and increases hydrophobic interactions (Hoekstra, et al., *J. Biol. Chem.*, 264:6786, 1989).

It is known that certain MPEG chelates can be effective iron chelators. For example, it is known that MPEG can be linked with iminodiacetate terminus (MIDA).

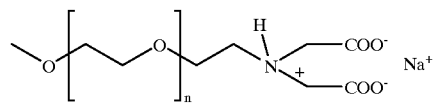

wherein n=3 to 8.

Other chelates modified with MPEG include MPEG 550-deferoxamine (ferrioxamine), prepared by reacting MPEG molecular weight 550 with carbonyldiimidazole, followed by reaction of the resulting imidazolecarbonyl ester with deferoxamine base, forming a urethane linkage. The material was produced as a chelate for gadolinium, to be used as a renal magnetic resonance contrast agent (Duewell, et al., *Invest. Radiol.*, 26:50, 1991). Deferoxamine is known to be an effective chelator for ferric iron.

MIDA can be prepared by converting MPEG 350 to the chloride by reaction with thionyl chloride according to Bueckmann et al., *Biotechnology & Applied Biochem.*, 9:258–268, 1987, and to the iminodiacetate by reaction of the chloride with sodium iminodiacetate (Wuenschell et al., *J. Chromatog.* 543: 345–354, 1991). The methyl ester can be prepared with methanolic HCl. However, alternative MPEG chelates, which are more effective chelators and are nontoxic, have been sought after.

SUMMARY OF THE INVENTION

The present invention is directed to methoxypolyethylene glycols (MPEG), which are modified by chemically attaching chelating groups onto the nonmethyl end of the polymer. Such chelating groups include ethylene-diamine tetraacetic acid (EDTA), diethylene triamine pentaacetic acid (DTPA), similar chelating compounds formed by reaction of bromoacetic acid or derivatives to triethylenetetramine and other higher homologs containing ethylenamine linkages (Bruenger et al. *J. Med. Chem.*, 35:112–118, 1992) and ethylene glycol aminoethyl ether tetraacetic acid (EGTA). The chelating groups may be in the form of a salt of physiologically acceptable cation or cations, an alkyl ester, or other suitable derivative of carboxylic acid. The methoxypolyethylene glycol may be linked to the chelate by an amine or amide linkage.

The present invention is directed to a derivative of methoxypolyethylene glycol having the formula (I):

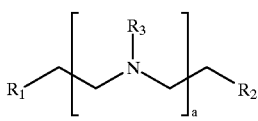

wherein $R_1$ and $R_2$ are independently selected from formulas (II) and (III):

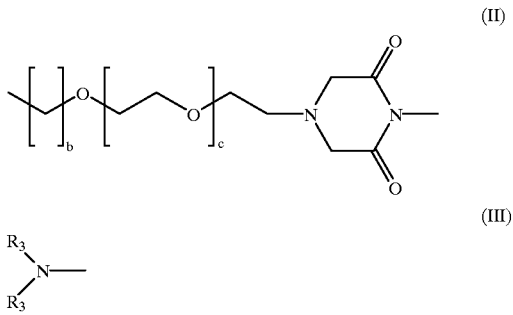

and each $R_3$ is independently selected from formula (IV)

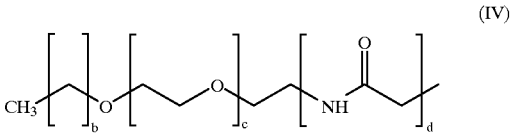

or selected from the group consisting of

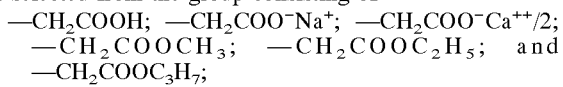

wherein a is 0 to 6, preferably 1 to 2; each b is independently 0 to 18, preferably 0; each c is independently 6 to 10, preferably 7–8; d is 0 to 1.

In particular, one embodiment of the present invention converts the terminal hydroxyl of MPEG to an amine, and then links the amine via an amide linkage with one of the carboxyl groups of ethylenediaminetetraacetate to produce methoxypolyethylene glycol amide of EDTA (MPEDTA).

A preferred embodiment of the present invention is the compound of formula (I) wherein a and each b are 0, each c is independently 6 to 10, d is 1, $R_1$ is formula III, one $R_3$ is formula (IV), two $R_3$'s are —$CH_2COO^-Ca^{++}/2$ and one $R_3$ is —$CH_2COO^-Na^+$.

A particularly preferred embodiment of the present invention is the compound of formula (I) when a is 1, each b is 0, each c is independently 6 to 10, preferably 7, d is 1, $R_1$ is formula (II), $R_2$ is formula (III), one $R_3$ is formula (IV), and two $R_3$'s are —$CH_2COOCH_3$, Another embodiment is the direct linkage of the methoxypolyethylene glycol to the chelate in an amine linkage, where d is 0.

These derivatives may be synthesized using methods known in the art such as from the methoxypolyethylene glycol chloride (Bueckmann et al., Biotechnology & Applied Biochem., 9:258–268, 1987) to the polyethyleneimine (Bruenger et al., J. Med. Chem., 35:112–118, 1992).

The present invention is also directed to a pharmaceutical composition comprising an effective amount of a formula (I) to reduce or prevent tissue damage from radiation or prevent renal or cardiac toxicity of doxorubicin, together with a pharmaceutically acceptable carrier.

The present invention is further directed to a method of preventing tissue damage during radiation treatments by administering to a patient in need thereof an effective amount of a compound of formula (I).

Further, the present invention is directed to a method of preventing renal toxicity during treatment of cancer by administering to a patient in need thereof an effective amount of a compound of formula (I).

In addition, the present invention is directed to a method of preventing cardiac toxicity of doxorubicin during treatment of cancer by administering to a patient in need thereof an effective amount of a compound of formula (I).

Additional advantages of the invention will be set forth in part in the description which follows, and in part will be apparent from the description, or may be learned by the practice of the invention. The advantages of the invention may be realized and obtained by means of the elements and combinations particularly pointed out in the claims.

It is to be understood that both the foregoing general description and the following detailed description are exemplary and explanatory only and are not restrictive of the present invention as claimed.

BRIEF DESCRIPTION OF THE DRAWINGS

FIG. 1A depicts the average scores after 30 Gy radiation of different treatment groups for radioprotection of compounds in mice.

FIG. 2 depicts the daily scores after 30 Gy radiation for different treatment groups for radioprotection of compounds in mice.

DETAILED DESCRIPTION OF THE INVENTION

Figure 1B:
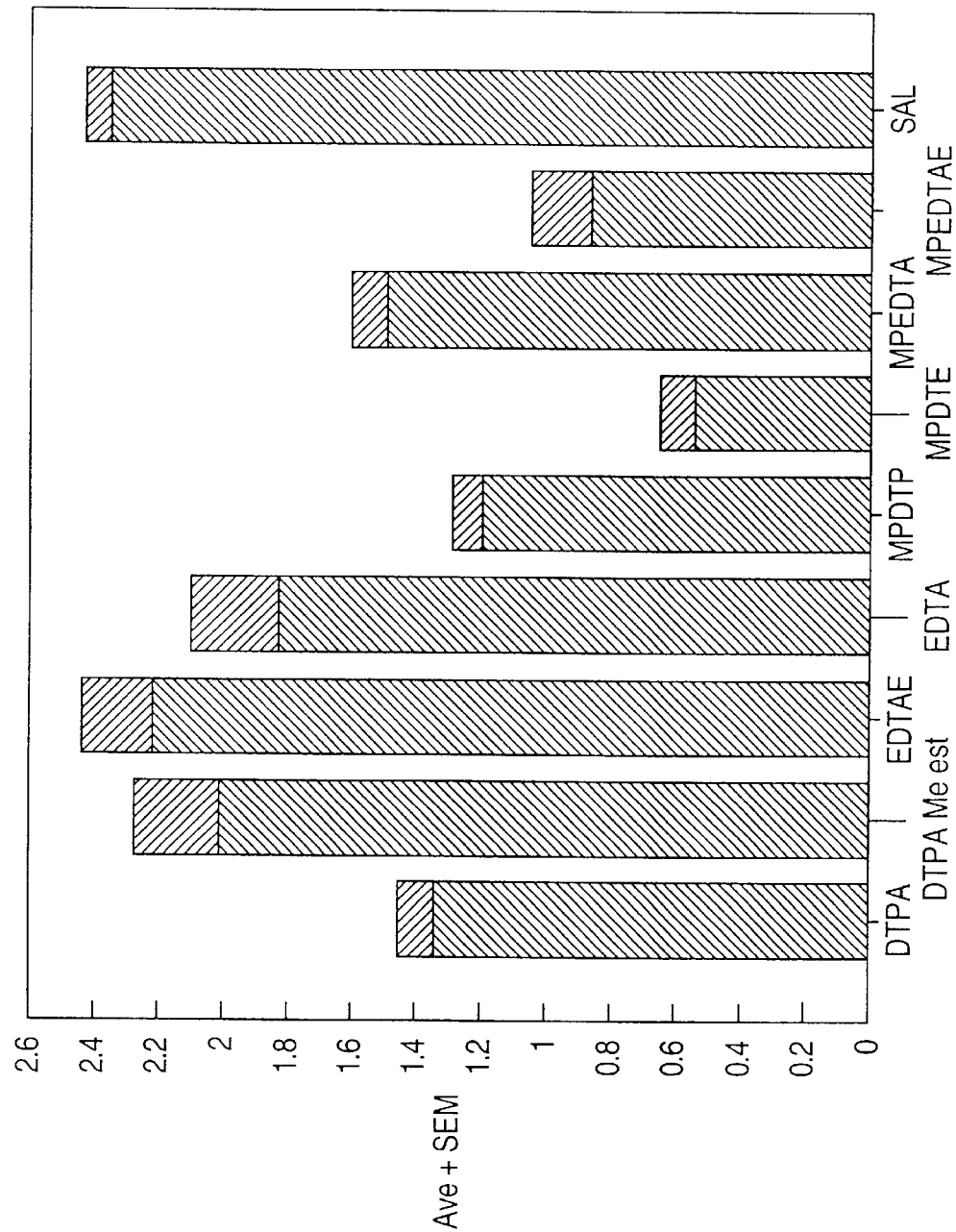
FIG. 1B depicts the average scores after 35 Gy radiation of different treatment groups for radioprotection of compounds in mice.

The compounds of the present invention are enhanced chelators in which the chelate is combined with low molecular weight PEG or other toxicity-lowering moiety. When administered to a patient, the compounds of the present invention reduce or prevent tissue damage during radiation treatments and preventing renal toxicity and/or cardiac toxicity of doxorubicin during treatment of cancer.

The present invention is directed to methoxypolyethylene glycols with an average weight of 200 to 600, and preferably 350 (MPEG 350), which are modified by chemically attaching chelating groups onto the nonmethyl end of the polymer by either an amide linkage or an amine linkage.

The chelating groups that can be used to modify the methoxypolyethylene glycols include ethylene diamine tetraacetic acid (EDTA), diethylene triamine pentaacetic acid (DTPA) or similar chelating compounds formed by reaction of bromoacetic acid or derivatives to triethylenetetramine and other higher homologs containing ethylenamine linkages, and ethylene glycol aminoethyl ether tetraacetic acid (EGTA).

Particular embodiments of the present invention are the chelators or prodrugs thereof obtained when methoxypolyethylene glycol amine (MPNH$_2$) is combined to form the amide with EDTA, and converted to the calcium sodium salt (MPEDTA), for example by mixing the carboxylic acid form of MPEDTA with appropriate quantities of calcium hydroxide and sodium hydroxide.

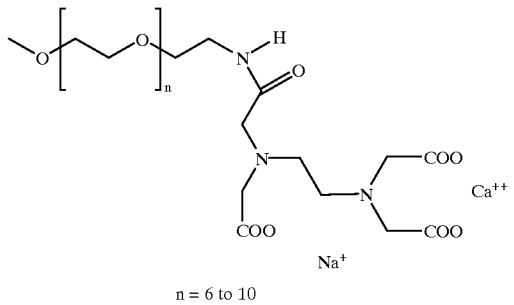

n = 6 to 10

Alternatively, one or two molecules of MPNH$_2$ are combined to form a mixture of amides including cyclic diketopiperazines with diethylenetriaminepenitaacetic acid (DTP), and converted to the methyl ester. The mixture is referred to as MPDTE, where c is preferably 7–8.

MPEDTA can be produced, for example, by first converting MPEG 350 to the chloride by reaction with thionyl chloride, then to an amine by reaction of the chloride with ammonia (Bueckmann et al., Biotechnology & Applied Biochem., 9:258–268, 1987), and then coupling the amine with ethylenediamine tetraacetate monoanhydride (Takeshita et al., *J. Am. Oil Chem. Soc.*, 59: 104, 1982).

MPEDTA can be produced by any standard method for amide formation, including the following: EDTA anhydride can be reacted with an amine in 0.3 M HEPES buffer at room temperature to form the amide (Lin et al., *Biochemistry*, 28:1054, 1989). EDTA in excess plus the amine in dimethylformamide at 120 degrees results in the amide (Hertzberg et al., *J. Am. Chem. Soc.*, 104:313, 1982). EDTA triethyl ester plus the amine, in dimethylformamide at 120 degrees results in the amide, and EDTA triester plus carbonyl diimidazole in dimethylformamide at room temperature, followed by the addition of amine, result in the amide (Hertzberg et al., *Biochemistry*, 23:3934, 1984). EDTA triester, an amine, and dicycloxexylcarbodiimide react to form the amide (Yanagisawa et al., *Prostaglandins*, 31:1063, 1986). EDTA triester, an amine, ethyldimethylaminopropylcarbodiimide, and dimethylaminopyridine as a catalyst result in formation of the amide (Mazzarelli et al., *Biochemistry*, 32:2979, 1993). Another method employed the cobaltic salt of EDTA which left one free carboxyl group to react with an amine in water catalyzed by ethyl-3-dimethylaminopropylcarbodiimide (Haner et al., *Arch. Biochem. Biophys.*, 231:477, 1984). The cobalt was later removed by extraction with dithizone in CCl$_4$.

MPDTE can be produced in the same manner as MPEDTA by substituting the appropriate derivative of diethylenetriaminepentaacetic acid (DTPA) for EDTA. Alternatively, the product may be prepared by reacting the amine of methoxypolyethylene glycol (Bueckmann et al., Biotechnology & Applied Biochem., 9:258–268, 1987) with DTPA in the presence of dicyclohexylcarbodiimide (Sheehan et al., J. Am Chem Soc 77:1067, 1953).

MPEDTA is very effective in reducing or preventing damage from radiation or doxorubicin. MPDTE is particularly effective in preventing tissue damage during radiation treatments.

While it may be possible for MPEDTA or MPDTE to be administered as the raw chemical, it is preferable to use it as a pharmaceutical formulation. According to a further aspect, the present invention provides a pharmaceutical formulation comprising MPEDTA or MPDTE or a pharmaceutically acceptable salt, methyl ester, or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The present invention may be administered by the following routes: intravenous; intraarterial; intraperitoneal; intrathecal; intramuscular; oral; sublingual; buccal; aerosol (inhalant or topical); subcutaneous; nasal drops; eye drops; ear drops; topical (both direct and as patches, for use on skin and on internal organs); intracranial; intracardiac; suppository; intravaginal; extracorporeal (for dialysis, dosing blood organs, and perfusion solutions); and electroporetic. The most suitable route may depend upon, for example, the condition and disorder of the recipient.

The formulations may conveniently be presented in unit dosage form and may be prepared by any of the methods well known in the art of pharmacy. All methods include the step of bringing into association MPEDTA, MPDTE, or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers, or both, and then, if necessary, shaping the product into the desired formulation.

Formulations of the present invention suitable for oral administration may be presented as discrete units, such as capsules, cachets or tablets, each containing a predetermined amount of the active ingredient; as a powder or granules; as a solution or a suspension in an aqueous liquid or a non-aqueous liquid; or as an oil-in-water liquid emulsion. The active ingredients may also be presented as a bolus, electuary or paste.

A tablet may be made by compression or molding, optionally with one or more accessory ingredients. Compressed tablets may be prepared by compressing in a suitable machine the active ingredient in a free-flowing form, such as a powder or granules, optionally mixed with a binder, lubricant, inert diluent, lubricating, surface-active or dispersing agent. Molded tablets may be made by molding in a suitable machine a mixture of the powdered compound moistened with an inert liquid diluent. The tablets may optionally be coated or scored, and may be formulated so as to provide slow or controlled release of the active ingredient therein.

Formulations for parenteral administration include aqueous and non-aqueous sterile injection solutions which may contain antioxidants, buffers, bacteriostats, and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, saline or water-for-injection, immediately prior to use. Extemporaneous injection solutions and suspensions may be prepared from sterile powders, granules and tablets of the kind previously described.

Formulations for rectnl administration may be presented as a suppository with the usual carriers, such as cocoa butter or polyethylene glycol.

Formulations for topical administration in the mouth, for example buccally or sublingually, include lozenges comprising the active ingredient in a flavored basis, such as sucrose and acacia or tragacanth, and pastilles comprising the active ingredient in a basis, such as gelatin and glycerin or sucrose and acacia.

Preferred unit dosage formulations are those containing an effective dose, as hereinbelow recited, or an appropriate fraction thereof, of the active ingredient.

It should be understood that, in addition to the ingredients particularly mentioned above, the formulations of this invention may include other agents conventional in the art having regard to the type of formulation in question, for example those suitable for oral administration may include flavoring agents.

The present invention may be administered in the following doses: internal 1 pg/kg to 10 g/kg; topical 0.00001% to 100%, formulated as preparations for immediate or sustained release. The dosing regimens of the present invention include discrete doses of between 1 and 8 administrations per day, acute single dose, and chronic multiple dose, as drip (constant IV or other infusion), or as bolus. The invention may be formulated with solvent and other agents or compounds.

The precise amount of MPEDTA or MPDTE compound administered to a patient will be the responsibility of the attendant physician However, the dose employed will depend on a number of factors, including the age and gender of the patient, the precise disorder being treated, and its severity. Also, the route of administration may vary depending on the condition and its severity.

The compounds of the present invention are useful in the treatment and prevention of tissue injury mediated by free radicals. Free radicals can be produced from ionizing radiation, cardiac toxicity from certain drugs (e.g., doxorubicin, trauma, and ischemia-reperfusion of myocardial infarction and stroke.) A free radical component may also be involved in auto-inmnune, chronic inflammatory, and viral diseases.

Specifically, the present invention is also directed to a method of preventing tissue damage during radiation treatments. A patient in need thereof is given an effective amount of MPEDTA or MPDTE by any of the effective routes of administration.

The present invention is also directed to a method of preventing cardiac and renal toxicity of doxorubicin during treatment of cancer. A patient in need thereof is injected with an effective amount of MPEDTA or MPDTE.

EXAMPLES

The invention will be further described by reference to the following examples. These examples should not be construed in any way as limiting the invention.

The MPEG-linked chelates were tested biologically for maximum tolerated dose or LD 50, radioprotection, and protection against doxorubicin toxicity. Attachment of MPEG to IDA, EDTA, or DTPA results in derivatives that are of comparable toxicity to the parent compounds.

Comparative Example 1
Methoxypolyethylene Glycol Iminodiacetate (MIDA).

MPEG 350 was converted to the chloride by reaction with thionyl chloride, and to the iminodiacetate by reaction of the chloride with sodium iminodiacetate (Wuenschell, et al., *J. Chromatog.*, 543:345–354, 1991). The product was purified by charcoal decolorization, gel filtration and ion exchange chromatography. Viscous oil, yield 35–48%. The methyl ester was prepared with methanolic HCl. TLC (methanol) MIDA Rf 0.39, MIDA methyl ester Rf0.77. FAB MS (m-nitrobenzyl alcohol matrix) of the methyl ester m/z=396, 440, 484, 528, 572, and 616, with median peak height between 440 and 484, corresponding to MH$^+$ with n=5, 6, 7, 8, 9, and 10, and a second series m/z=418, 462, 506, 550, 594, and 638, median between 462 and 506, corresponding to MNa$^+$, with n=5, 6, 7, 8, 9, and 10. High resolution FAB MS, n=5, $C_{17}H_{34}O_9N$, MH$^+$ Calc. 396.2236. Found 396.2241. n=6, $C_{19}H_{38}O_{10}N$, MH$^+$ Calc. 440.2495. Found 440.2513. n=7, $C_{21}H_{42}O_{11}N$, MH$^+$ Calc. 484.2757. Found 484.2776. NMR of the methyl ester (400 MHZ, hexadeuteroacetone; ppm from tetramethylsilane): 2.91 (t,2, $CH_2CH_2N$) 3.28(s,3,$CH_3OCH_2$), 3.45–3.6 (mult,28), 3.62 (s,4,$NCH_2CO$), 3.64(s,6,$COOCH_3$).

Example 1
Methoxypolyethlene Glycol Amide with EDTA (MPEDTA).

MPEG 350 was first converted to the chloride by reaction with thionyl chloride, then to the amine by reaction of the chloride with ammonia (Bueckmann et al., Biotechnology & Applied Biochem., 9:258–268, 1987), and then the amine was coupled with ethylenediamine tetraacetate monoanhydride (Takeshita, et al., *J. Am. Oil Chem. Soc.*, 59:104, 1082). The product was purified by decolorizing charcoal, gel filtration, and ion exchange chromatography. Fractions containing product as assayed by titration with calcium and copper were pooled and lyophilized. Viscous oil, yield 25–30%. TLC (methoxyethanol:conc ammonium hydroxide 2:1) Rf. 0.55–0.7, Rf EDTA.4. FAB MS of the methyl ester m/z 568, 612, 656, 700, 744, and 788 with median peak height between 612 and 656, corresponding to MH$^+$, with n=5, 6, 7, 8, 9, and 10, and another series 590, 634, 678, 722, 766, and 810, with median peak height 678 corresponding to MNa$^+$, with n=5, 6, 7, 8, 9, and 10. High resolution FAB MS of methyl ester n=6 $C_{26}H_{50}O_{13}N_3$, MH$^+$ Calc. 612.3343. Found 612.3358. n=7, $C_{28}H_{54}O_{14}N_3$, MH$^+$ calc.656.3605. Found656.3597. NMR of methyl ester (400 MHZ hexadeuteroacetone, ppm). 2.82 ($A_2B_2M,4,NCH_2CH_2N$); 2.86 (br,1,NHCO); 3.18 (s,2,$NCOCH_2$); 3.28 (s,3,$CH_3O$); 3.36 (d of t,2,$CH_2CH_2NHCO$); 3.44–3.66 (mult, 43). For comparison, the NMR of the methyl ester of EDTA 2.82(s, 4,$NCH_2CH$ $N_2$), 3.61(s,8,$NCH_2CO$), 3.63(s,12,COOCH, and the NMR of MPEG 3.38(s,3), 3.6–3.7(mult,28).

Example 2
Metyl Ester of MPEDTA, (MPEDTAE)

This compound was prepared by Fischer esterification of MPEDTA, and purified by Bio-Gel P2 chromatography.

Example 3
Methoxypolyethyene Glycol Amide with DTPA. Methyl Ester of (MPDTE)

Methoxypolyethyene glycol amine, prepared as described above, is converted to an amide or amides with diethylentriaminepentaacetic acid by reaction in the presence of dicyclohexyldarbodiimide, triethylamine, and dimethylformamide (Sheehan et al., *J. Am Chem. Soc.* 77:1067, 1953). The solvent was evaporated, the mixture taken up in water, treated with charcoal and filtered. The product was purified by extraction into butanol from 5M potassium carbonate solution, and by chromatography on a Bio-Gel P2 column with elution by water. The ester was formed by Fischer esterification, by reaction of the anhydrous product with methanolic hydrochloric acid. The yield was about 25%. The product was assayed by thin layer chromatography (TLC), NMR, and by titration with cupric ions after saponification. TLC silica gel, (ethyl acetate:methanol:conc ammonium hydroxide::4:1:1) Rf=0.81, 0.88. NMR (400 MHZ, $D_2O$, ppm) 2.78 (broad multiplet, 8, $NCH_2CH_2N$); 3.37 (s,9, $CH_3OCO$); 3.5–3.8 (multiple peaks, 82, methoxypolethylene, NCH2CO) Total 99 protons. For MPDTE with two R2 and three R3 groups, n average=7, formula=$C_{51}H_{99}N_5O_{24}$. Molecular weight calc 1165. The dried weighed product was saponified with sodium hydroxide to the carboxylate form, and titrated with copper to determine the molecular weight (Blijenberg et al., *Clin, Chim. Acta* 26:577–579, 1969). Molecular weight found 1194+–50. The mixture of products designated MPDTE contained in addition, another product, the cyclic amide, with formula I, $R_1$ is formula II, $R_2$ is formula III, two of $R_3$ are —$CH_2COOCH_3$, and the remaining $R_3$ is formula IV with b=0, c=7 to 10, d=1. FAB mass spectrum molecular mass for c=9, 1223. Found 1223.

Example 4

Methoxypolyethyene Glycol Amide with DTPA. Calcium Sodium Salt (MPDTP)

The product of Example 3 before esterification was converted to the calcium sodium salt by adding an equivalent quantity of calcium hydroxide and sodium hydroxide, and bringing the pH to 7 by addition of hydrochloric acid.

TOXICITY STUDIES

For all biological studies, the substances were dissolved in water and brought to pH 7. In the case of EDTA and MPEDTA, the calcium salts were used. Preliminary determination of the approximate toxicity level of the substances was by intraperitoneal (IP) injection of increasing doses into individual Swiss-Webster female mice until toxicity was evident. The maximum tolerated dose was the highest dose given without evident toxic symptoms such as coma, convulsions, or death. The LD 50 (IP) was determined by using at least three doses in 12 mice at each level, bracketing the approximate LD 50. The mice were followed for at least one week and examined for weight changes, general condition, and behavior. The LD 50 with lower and upper confidene iits was calculated from the data. The LD 50 (millimoles per kiilogram) with lower and upper limits (LL and UL) for the substances and for parent compounds EDTA, iminodiacetate (IDA), DTPA, an d MPEG are shown in Table I.

TABLE I

LD50 of Compounds Intraperitoneally in Mice

| Compound | Mol Wt | mmole/kg LL | mmole/kg LD50 | mmole/kg UL | mmole/kg MTD[b] |
|---|---|---|---|---|---|
| MPEG | 350[a] | 31.4 | 35.7 | 407 | 18 |
| EDTA ($Na_2Ca$) | 374 | 15.2 | 17.0 | 19.0 | 8 |
| IDA(Na) | 155 | 30.5 | 33.1 | 36.1 | 17 |
| MPEDTA(NaCa)* | 646[a] | 11.4 | 12.5 | 13.0 | 8 |
| MIDA(Na) | 477[a] | 18.1 | 20.6 | 23.3 | 8 |
| DTPA(NaCa) | 484 | — | — | — | 8 |

TABLE I-continued

LD50 of Compounds Intraperitoneally in Mice

| Compound | Mol Wt | mmole/kg LL | mmole/kg LD50 | mmole/kg UL | mmole/kg MTD[b] |
|---|---|---|---|---|---|
| MPDTE* | 1165[a] | — | — | — | 2 |
| DTPA methyl ester[c] | 463 | — | — | — | 1 |

*Inventive compound
[a]Approximate average mol wt. Mixture of homologs of MPEG with average n = 7
[b]MTD = maximum tolerated dose
[c]Prepared by Fischer esterification of DTPA with methanolic hydrochloric acid From Table I, it is apparent that attachment of MPEG to IDA, EDTA, or DTPA results in derivatives that are of comparable toxicity to the parent compounds. The ester MPDTE toxicity was also comparable with the corresponding ester of DTPA.

RADIOPROTECTION STUDIES

The effect of PEG derivatives on tissue tolerance to radiation was tested. Groups of 6 or 12 female Swiss-Webster mice were given IP solutions of the derivatives at a dose of approxfimately one-half of the LD50. Ten minutes later, pentobarbital (PB) 0.262 mmole/kg was given IP, and twenty minutes after the first injection, the right hind leg only was irradiated with 30, 35 or 40 Gy using the Philips RT-250 unit operated under the following conditions: 200 kVp, 20 mA, 0.2 mm Cu added filtration, HVL 0.57 mm Cu, dose rate of 1.834 Gy/min. Mice were irradiated in groups of 6 or 12, and their legs were arranged within a 20×24 cm aperture cone at a 50 cm target-to-skin distance such that all their legs were within a 95% isodose. The output of the X-ray unit was calibrated using a Capintec PT-06C Farmer chamber. Controls received only PB and 0.4 ml normal saline in place of the drug.

Figure 1C:
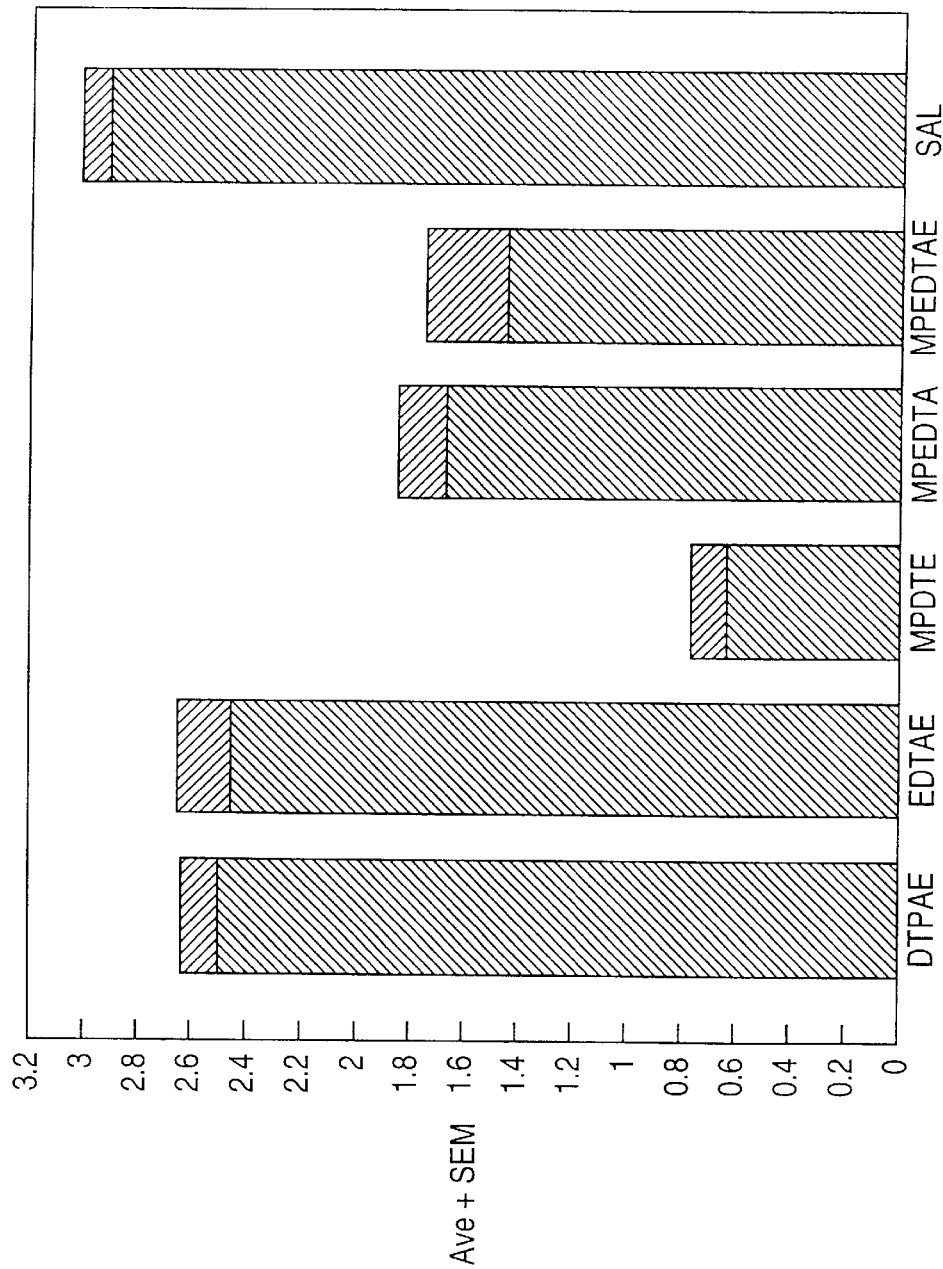
FIG. 1C depicts the average scores after 40 Gy radiation of different treatment groups for radioprotection of compounds in mice.

The mice were examed daily by two independent observers for 24 days, and the limbs were scored for radiation damage graded on a scale of 0 to 3.5 according to criteria previously established (Fowler, et al., *Int. J. Rad. Biol.*, 9:241–252, 1964). Briefly, a score of 1 corresponds to definite reddening of the foot compared to normal and a score of 2 is marked moist desquamation, loss of hair and skin, and sticking together of toes. In the control irradiated mice given saline, the irradiated limbs began to show evidence of tissue damage at day 12, reaching a maximum average score on day 16–18, and gradually healing thereafter. The average scores in the different treatment groups for days 12–24 are shown in Tables II and III, and FIGS. 1A, 1B and 1C, and the daily scores in FIG. 2.

TABLE II

Radioprotection of Compounds in Mice. Average scores day 12–24, 12 mice in each group. 30 Gy to right limb.

| Compound | mmole/kg | Av Score | SEM |
|---|---|---|---|
| Saline | — | 1.54 | 0.53 |
| IDA | 16.7 | 1.19 | 0.32 |
| EDTA | 8.6 | 0.67 | 0.27 |
| MPEG | 17.9 | 0.65 | 0.26 |
| MIDA | 10.3 | 0.67 | 0.34 |
| MPEDTA | 7.7 | 0.24 | 0.26 |

TABLE III

Radioprotection of Compounds in Mice.
Average scores day 15–20, 6 mice in each
group. EDTAE, DTPAE are methyl esters of EDTA and DTPA,
respectively.

| Compound | mmole/kg | Av score | SEM | Rad dose, Gy |
|---|---|---|---|---|
| Saline | — | 2.36 | 0.08 | 35 |
| EDTA | 8.0 | 1.83 | 0.26 | 35 |
| DTPA | 8.0 | 1.34 | 0.11 | 35 |
| MPEDTA | 8.0 | 1.50 | 0.11 | 35 |
| EDTAE | 1.0 | 2.21 | 0.23 | 35 |
| MPEDTAE | 2.0 | 0.88 | 0.18 | 35 |
| MPDTP | 8.0 | 1.21 | 0.16 | 35 |
| MPDTE | 2.0 | 0.55 | 0.11 | 35 |
| Saline | — | 2.93 | 0.10 | 40 |
| EDTAE | 1.0 | 2.46 | 0.20 | 40 |
| MPEDTAE | 2.0 | 1.45 | 0.30 | 40 |
| MPEDTA | 8.0 | 1.67 | 0.18 | 40 |
| DTPA ester | 1.0 | 2.50 | 0.14 | 40 |
| MPDTE | 1.0 | 0.63 | 0.13 | 40 |

The results of ANOVA (analysis of variance) indicated that the average score of the saline group was significantly greater than that of all of the other groups, and the MPDTE scores were significantly lower than that of all of the other groups. There was little difference between EDTA, MPEG, and MIDA groups. In sum, IDA and DTPA each were slightly effective as radioprotectants, EDTA, DTPA, MPEG, and MIDA were moderately effective, and MPEDTA and MPDTE were extremely effective, particularly the MPDTE, which surpassed all tested substances in protection even against 40 Gy radiation to the limb. MPEDTAE was also effective in protection from tissue injury, whereas the esters of EDTA and DTPA were not effective, indicating the requirement for the methoxypolyethylene glycol linkage to the chelate group.

EFFECT ON RENAL TOXICITY OF DOXORUBICIN

Figure 3:
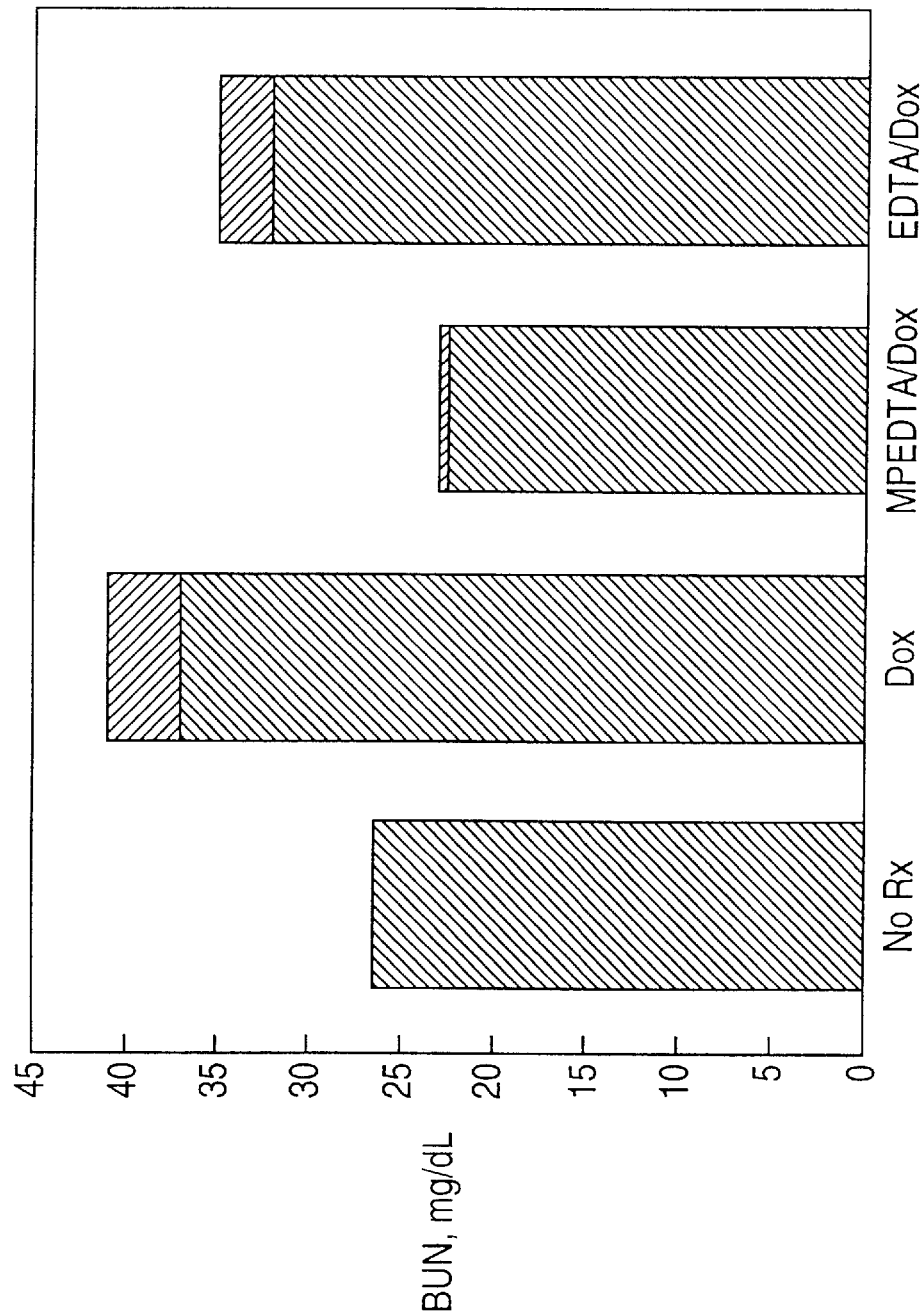
FIG. 3 depicts doxorubicin treatment results for different treatment groups.

Although the efficacy of doxorubicin in the treatment of cancer is due to its binding with DNA, the toxic side effects are due to promotion of free radical reactions that result in cardiac and renal damage (Myers, et al., Science, 197:165, 1977). MPEDTA and EDTA were tested in mice for possible protection against the cardiac damage and renal toxicity of doxorubicin. Groups of 6 mice were injected with either saline, EDTA 7 mmole/kg, or MPEDTA 7 mmole/kg IP, followed one hour later by 25 mg/kg doxorubicin into the tail vein. The mice were followed for weight change and general condition for 27 days, after which the blood urea nitrogen levels (BUN) were determined. The mean and SEM of the different treatment groups are shown in FIG. 3. Doxorubicin treatment resulted in markedly increased BUN compared with the untreated control group. This was completely prevented by MPEDTA, but not EDTA treatment, reflecting the enhanced effectiveness of the novel compound.

EFFECT ON DOXORUBICIN-CAUSED TUMOR GROWTH LAG

Figure 4:
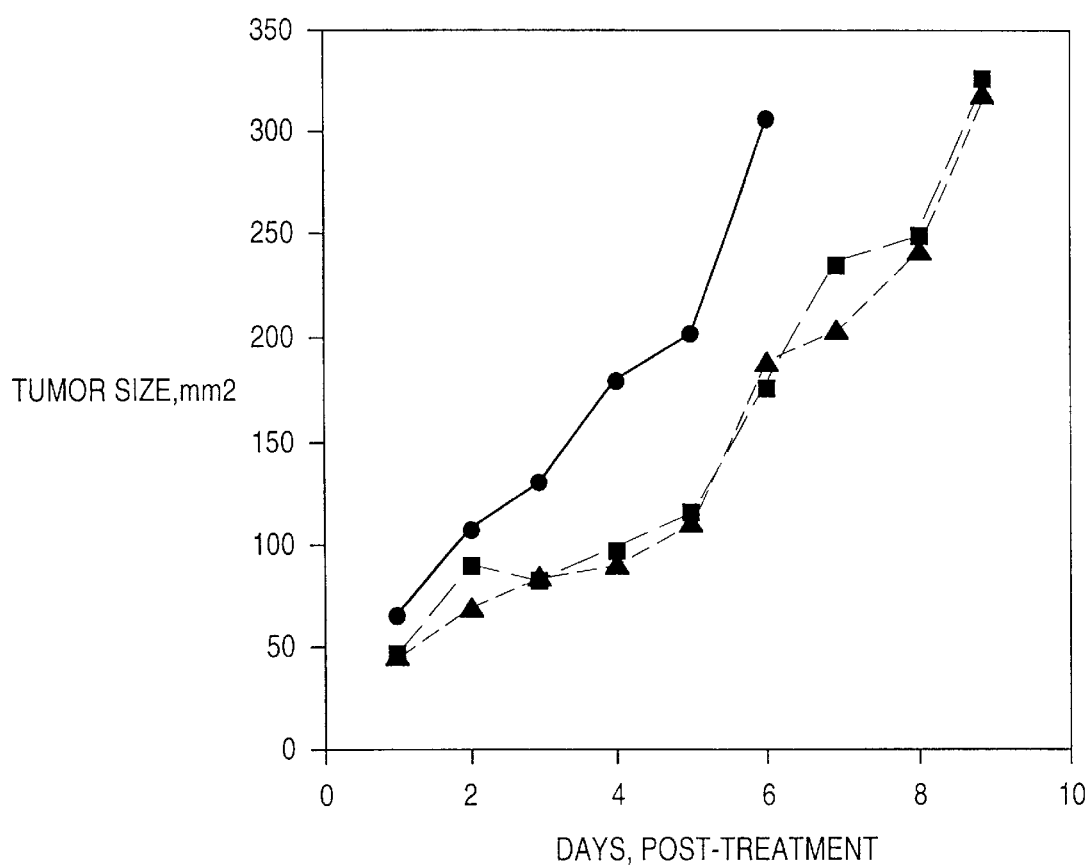
FIG. 4 depicts the lack of effect of MPEDTA on tumor growth lag produced by doxorubicin.

For this assay, the B16F1 malignant melanoma which grows in isologous C57Bl/6 mice was used. The subcutaneous injection of one million cells (grown in cell culture from frozen stores) into the back of the mice resulted in formation of tumors that were palpable within 7–10 days post injection. When the tumors reached an average of 6–8 mm diameter, they were placed in closely matched groups of 12 with similar average size tumors. The groups were injected intraperitoneally with either saline or MPEDTA, followed 30 minutes later by doxorubicin 15 mg/kg IP or saline. Tumor volumes were assessed by daily caliper measreients m two orthogonal planes. Tumor length is defined as the diameter in the plane parallel to the body, while width is defined as the diameter perpendicular to the body. Diameter product (in $mm^2$) was used as the index of tumor growth. The tumor areas were averaged and plotted vs. time to show growth delay as a function of the various treatments. When the average area reached 300 nm2, the mice were killed by cervical dislocation. The results are in FIG. 4. The solid circles indicate the groups receiving saline-saline or MPEDTA-saline, the solid squares indicate the group receiving saline-doxorubicin, and the solid triangles indicate the group receiving MPEDTA-doxorubicin. The MPEDTA clearly did not interfere with the tumoricidal effect of doxorubicin.

EFFECT ON DOXORUBICIN-INDUCED HEART DAMAGE

Figure 5:
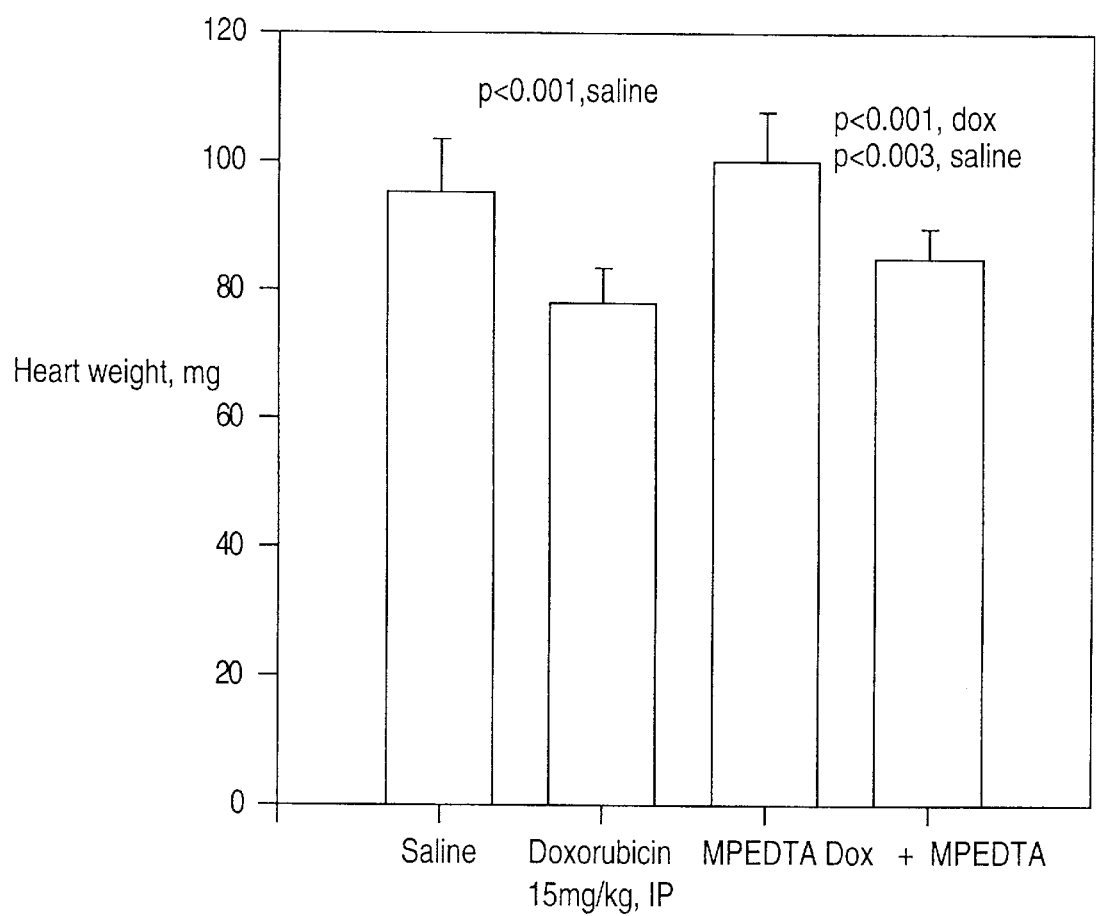
FIG. 5 depicts the protection by MPEDTA against heart weight loss caused by doxorubicin.

Experiments were carried out similarly to the tumor growth lag studies, except that nontumor-bearing C57BL/6 mice were used. Groups of 12 mice were injected with either saine—saline, saline-doxorubicin, MPEDTA-saline, or MPEDTA-doxorubicin, followed for 28 days, and tissues taken for study. A striking indication of cardiac toxicity was loss of heart weight in mice receiving doxorubicin. Results are summarized in FIG. 5. Doxorubicin alone caused a significant heart weight loss, which was partially prevented by the single dose of MPEDTA. MPEDTA alone was similar to the saline control. Thus, MPEDTA reduced the cardiac damage caused by doxorubicin. The new chelates described here have been shown to possess similar toxicity to parent compounds, and have been found to be potentially useful in reducing damage from radiation and doxorubicin, and, by implication, other disorders due to free radicals. The compounds may be useful in other clinical situations requiring chelation, such as iron-overload diseases, including thalassemia, sickle-cell disease, and hemochromatosis, and in the treatment of lead, mercury, or other heavy metal poisoning.

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A derivative of methoxypolyethylene glycol, comprising one or more methoxypolyethylene glycols terminated in amide or amine linkages to ethylenediamine, diethylenetriamine, or polyethyleneimines, in which remaining nitrogen bonds are covalently linked to the alpha carbon of acetic acid residues, the carboxylate groups being in the form of a free acid, an ion with a pharmacologically acceptable counter-ion, or an alkyl ester, wherein the derivative has the following formula (I)

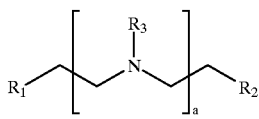

wherein one of $R_1$ and $R_2$ is formula (III) and the other is selected from formulas (II) and (III):

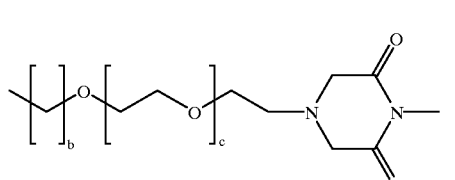

and one $R_3$ is formula (IV) and each of the remaining $R_3$ is independently selected from formula (IV)

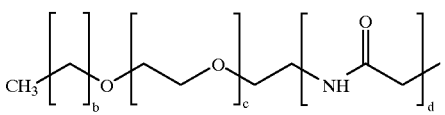

or from the group consisting of
—$CH_2COOH$; —$CH_2COO^-Na^+$; —$CH_2COO^-Ca^{++}/2$; —$CH_2COOCH_3$; —$CH_2COOC_2H_5$; and —$CH_2COOC_3H_7$;
wherein a is 0 to 6; each b is independently 0 to 18; each c is independently 6 to 10; and d is 0 to 1.

2. The derivative according to claim 1, wherein formula (I) is methoxypolyethylene glycol amide of ethylene diamine tetracetic acid.

3. The derivative according to claim 1 wherein a and each b are 0, each c is independently 6 to 10, d is 1, $R_1$ is formula III, one $R_3$ is formula IV, two $R_3$'s are —$CH_2COO^-$ $Ca^{++}/2$ and one of $R_3$ is —$CH_2COO^-Na^+$.

4. The derivative according to claim 1 wherein a is 1, each b is 0, each c is independently 6 to 10, and d is 1, $R_1$ is formula (II), $R_2$ is formula (III), one $R_3$ is formula IV, and two $R_3$'s are $CH_2COOCH_3$.

5. A p maceutical composition comprising an effective amount of a derivative as recited in claim 1 to reduce or prevent tissue damage from radiation or prevent renal or cardiac toxicity of doxorubicin, together with a pharmaceutically acceptable carrier.

6. A pharmaceutical composition comprising an effective amount of a derivative as recited in claim 3 to reduce or prevent tissue damage from radiation or prevent renal or cardiac toxicity of doxorubicin, together with a pharmaceutically acceptable carrier.

7. A pharmaceutical composition comprising an effective amount of a derivative as recited in claim 4 to reduce or prevent tissue damage from radiation, together with a pharmaceutically acceptable carrier.

8. The derivative according to claim 1, wherein each c is independently 7 to 8.

9. A method of preventing tissue damage during radiation treatments, comprising administering to a patient in need thereof with an effective amount of a derivative of methoxypolyethylene glycol, comprising one or more methoxypolyethylene glycols terminated in amide or amine linkages to ethylenediamine, diethylenetriamine, or polyethyleneimines, in which remaining nitrogen bonds are covalently linked to the alpha carbon of acetic acid residues, the carboxylate groups being in the form of a free acid, an ion with a pharmacologically acceptable counter-ion, or an alkyl ester, wherein the derivative has the following formula (I)

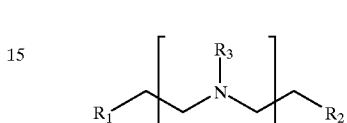

wherein $R_1$ and $R_2$ are independently selected from formulas (II) and (III);

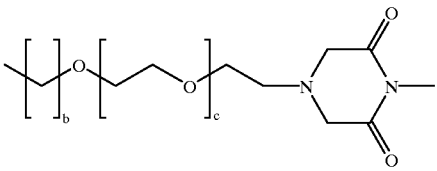

and each $R_3$ is independently selected from formula (IV)

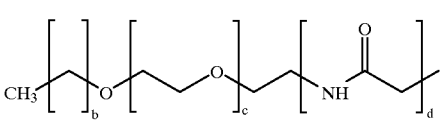

or from the group consisting of
—$CH_2COOH$; —$CH_2COO^-Na^+$; —$CH_2COO^-Ca^{++}/2$; —$CH_2COOCH_3$; —$CH_2COOC_2H_5$; and —$CH_2COOC_3H_7$;
wherein a is 0 to 6; each b is independently 0 to 18; each c is independently 6 to 10; and d is 0 to 1.

10. The method of preventing tissue damage during radiation treatments according to claim 9 wherein a and each b are 0, each c is independently 6 to 10, d is 1, $R_1$ is formula (III), one $R_3$ is formula (IV), two $R_3$'s are —$CH_2COO^-$ $Ca^{++}/2$ and one of $R_3$ is —$CH_2COO^-Na^+$.

11. The method of preventing tissue damage during radiation treatments according to claim 9 wherein a is 1, each b is 0, each c is independently 6 to 10, and d is 1, $R_1$ is formula (II), $R_2$ is formula (III), one $R_3$ is formula (IV), and two $R_3$'s are $CH_2COOCH_3$.

12. A method of preventing renal toxicity of doxorubicin during treatment of cancer, comprising administering to patient in need thereof an effective amount of a derivative of methoxypolyethylene glycol, comprising one or more methoxypolyethylene glycols terminated in amide or amine linkages to ethylenediamine, diethylenetriamine, or polyethyleneimines, in which remaining nitrogen bonds are covalently linked to the alpha carbon of acetic acid residues, the carboxylate groups being in the form of a free acid, an ion with a pharmacologically acceptable counter-ion or an alkyl ester, wherein the derivative has the following formula (I)

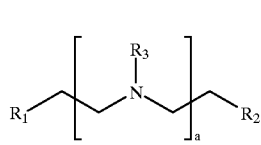
(I)

wherein $R_1$ and $R_2$ are independently selected from formulas (II) and (III):

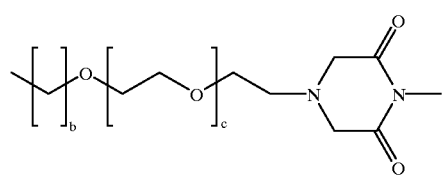
(II)

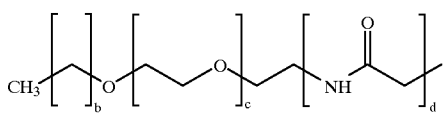
(III)

and each $R_3$ is independently selected from formula (IV)

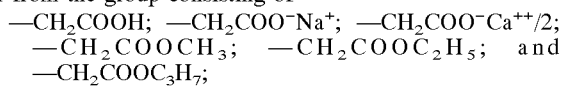
(IV)

or from the group consisting of
—$CH_2COOH$; —$CH_2COO^-Na^+$; —$CH_2COO^-Ca^{++}/2$; —$CH_2COOCH_3$; —$CH_2COOC_2H_5$; and —$CH_2COOC_3H_7$;
wherein a is 0 to 6; each b is independently 0 to 18; each c is independently 6 to 10; and d is 0 to 1.

13. A method of preventing renal toxicity of doxorubicin during treatment of cancer according to claim 12 wherein a and each b are 0, each c is independently 6 to 10 d is 1, $R_1$ is formula (III) one $R_3$ is formula (IV), two $R_3$'s are —$CH_2COO^-Ca^{++}/2$ and one of $R_3$ is —$CH_2COO^-Na^+$.

14. A method of preventing cardiac toxicity of doxorubicin during treatment of cancer, comprising administering to a patient in need thereof an effective amount of a derivative of methoxypolyethylene glycol, comprising one or more methoxypolyethylene glycols terminated in amide or amine linkages to ethylenediamine, diethylenetriamine, or polyethyleneimines, in which remaining nitrogen bonds are covalently linked to the alpha carbon of acetic acid residues, the carboxylate groups being in the form of a free acid, an ion with a pharmacologically acceptable counter-ion, or an alkyl ester, wherein the derivative has the following formula (I)

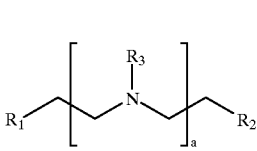
(I)

wherein $R_1$ and $R_2$ are independently selected from formulas (II) and (III):

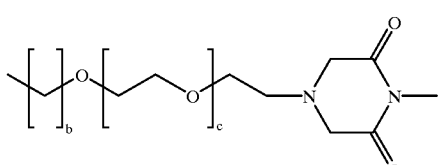
(II)

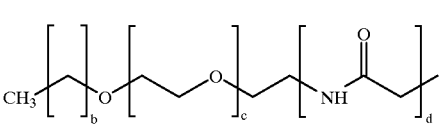
(III)

and each $R_3$ is independently selected from formula (IV)

(IV)

or from the group consisting of
—$CH_2COOH$; —$CH_2COO^-Na^+$; —$CH_2COO^-Ca^{++}/2$; —$CH_2COOCH_3$; —$CH_2COOC_2H_5$; and —$CH_2COOC_3H_7$;
wherein a is 0 to 6; each b is independently 0 to 18; each c is independently 6 to 10; and d is 0 to 1.

15. A method of preventing cardiac toxicity of doxorubicin during treatment of cancer according to claim 14 wherein a and each b are 0, each c is independently 6 to 10, d is 1, $R_1$ is formula (III), one $R_3$ is formula (IV), two $R_3$'s are —$CH_2COO^-Ca^{++}/2$ and one of $R_3$ is —$CH_2COO^-Na^+$.

* * * * *